United States Patent [19]

Woltersdorf, Jr. et al.

[11] 4,272,537

[45] Jun. 9, 1981

[54] 3-AMINO-5-SUBSTITUTED-6-HALO-N-(4,4-DISUBSTITUTED-6-SUBSTITUTED-1,3,5-TRIAZIN-2-YL)-2-PYRAZINECARBOXAMIDES

[75] Inventors: Otto W. Woltersdorf, Jr., Chalfont; S. Jane deSolms, Norristown; Robert L. Smith, Lansdale, all of Pa.

[73] Assignee: Merck & Co., Inc., Rahway, N.J.

[21] Appl. No.: 165,313

[22] Filed: Jul. 2, 1980

[51] Int. Cl.³ ............... C07D 403/12; A61K 31/495; A61K 31/53

[52] U.S. Cl. ................................. 424/249; 544/207; 544/242

[58] Field of Search ................ 544/207, 212; 424/249

[56] References Cited

U.S. PATENT DOCUMENTS

| | | | |
|---|---|---|---|
| 3,840,538 | 10/1974 | Hubele | 544/212 |
| 4,085,211 | 4/1978 | Cragoe et al. | 424/250 |

*Primary Examiner*—John M. Ford
*Attorney, Agent, or Firm*—Raymond M. Speer; Michael C. Sudol, Jr.

[57] ABSTRACT

This invention relates to 3-amino-5-substituted-6-halo-N-(4,4-disubstituted-6-substituted-1,3,5-triazin-2-yl)-2-pyrazinecarboxamides and processes for preparing same. The compounds are eukalemic/saluretic agents useful in the treatment of edema and hypertension.

11 Claims, No Drawings

3-AMINO-5-SUBSTITUTED-6-HALO-N-(4,4-DISUBSTITUTED-6-SUBSTITUTED-1,3,5-TRIAZIN-2-YL)-2-PYRAZINECARBOXAMIDES

BACKGROUND OF THE INVENTION

The background to this invention, U.S. Pat. No. 3,313,813 patented Apr. 11, 1967 and issued to Edward J. Craoge, Jr., shows novel (3-amino-5,6-disubstituted-pyrazinoyl)guanidine compounds. The compounds of the '813 patent are useful because they possess diuretic and natriuretic properties. They differ from most of the known, effective diuretic agents, however, in that the compounds of the '813 patent selectively enhance the excretion of sodium ions while simultaneously causing a decrease in excretion of potassium ions. The potassium loss, which is caused by known diuretics, often results in a severe muscular weakness. Since the compounds of the '813 patent prevent the potassium depletion, they have this decided advantage as diuretics. As diuretic agents, they can be used for the treatment of edema, hypertension and other diseases or conditions known to be responsive to this therapy and are especially useful when used in combination with or concomitantly with potassium losing diuretic agents.

It has been found in U.S. Pat. No. 3,313,813 that the pyrazinoylguanidine compounds therein described when co-administered with other diuretic agents known to enhance the elimination of potassium ions along with sodium ions, will maintain the potassium ion excretion at approximately the normal or control rate and thus overcome this undesirable property of other diuretic agents.

In actuality, applicants' compounds in the instant case as further described, accomplish the objective previously achieved by using a combination of pyrazinoylguanidine compounds of the U.S. Pat. No. 3,313,813 with diuretic agents which cause elimination of sodium with concomitant excessive potassium elimination. Thus, the compounds of the instant case are effective eukalemic/saluretic agents. Since the compounds of the instant invention are thus eukalemic/saluretic agents, they constitute single entities which are useful for the treatment of edema and hypertension and other diseases or conditions known to be responsive to this therapy.

SUMMARY OF THE INVENTION

The instant case covers novel 3-amino-5-substituted-6-halo-N-(4,4-disubstituted-6-substituted-1,3,5-triazin-2-yl)-2-pyrazinecarboxamides and processes for making the same. The novel compounds of this invention are depicted in Formula I below:

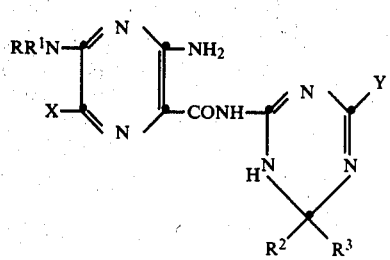

wherein
R and $R^1$ are the same or different and are hydrogen or $C_{1-5}$ alkyl, $C_{2-5}$ alkenyl or $C_{3-6}$ cycloalkyl;

$R^2$ and $R^3$ are the same or different and are $C_{1-5}$ alkyl;
$R^2$ and $R^3$ may also be joined with the carbon atom to which they are attached to form a 3-7 membered carbon ring;
X is halo such as chloro, fluoro, bromo or iodo;
Y is OH, SH, $C_{1-5}$ alkoxy, $C_{1-5}$ alkylthio and $NR^4R^5$ wherein $R^4$ is hydrogen or $C_{1-5}$ alkyl and $R^5$ is hydrogen, $C_{1-5}$ alkyl, CN, $CONH_2$,

$NO_2$ or $NH_2$ and the pharmaceutically acceptable acid addition salts thereof.

The invention includes compounds which are the tautomeric form of the compounds of Formula I namely to tautomeric forms of the formula:

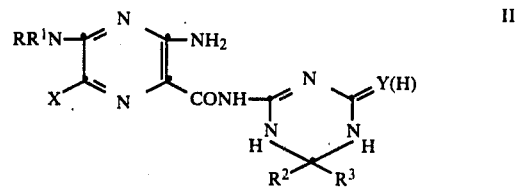

wherein R, $R^1$, X, $R^2$, $R^3$, $R^4$ and $R^5$ are as defined for Formula I and Y is as defined above minus a hydrogen atom.

In the above compounds, $C_{1-5}$ alkyl means both branched chain and straight chain radicals such as methyl, ethyl, propyl, isopropyl, butyl, pentyl, isopentyl and the like. $C_{2-5}$ alkenyl is represented by allyl, propenyl and the like and $C_{3-6}$ cycloalkyl is represented by cyclopropyl, cyclopentyl, cyclohexyl and the like.

Preferred compounds of this invention are those compounds of Formula I and the tautomeric form of Formula II wherein
R and $R^1$ are hydrogen or $C_{1-5}$ alkyl,
$R^2$ and $R^3$ are methyl,
X=Cl,
Y=OH, SH, $C_{1-5}$ alkoxy, $C_{1-5}$ alkylthio or cyanoamino and the pharmaceutically acceptable salts thereof.

The compounds of this invention as shown by Formula I and the preferred compounds discussed above are useful because they possess diuretic and natriuretic properties. In addition, they are useful eukalemic saluretics, in other words, the compounds of the instant case cause neither loss or abnormal retention of potassium ions. In contradistinction, the pyrazinoylguanidine compounds of U.S. Pat. No. 3,313,813 do cause a decrease in the excretion of potassium ions. However, other well known diuretics such as furosemide, chlorthalidone and acetazolamide cause an increase in potassium excretion which often results in muscular weakness. Applicants' compounds combine in a single agent the advantages of a combination of the known pyrazinoylguanidine diuretics of U.S. Pat. No. 3,313,813 which decrease potassium with the known diuretics which cause a potassium loss. Thus, the compounds of this invention maintain the excretion of potassium at approximately normal levels while causing an increased renal elimination of sodium ions and water which is the desirable characteristic of the diuretic.

Also covered within the scope of the above Formula I compounds and the preferred compounds are the pharmaceutically acceptable acid addition salts thereof. These salts can be made by reacting the free base with a pharmaceutically acceptable acid such as for example, hydrochloric acid, sulfuric acid, hydrobromic acid or isethionic acid. These salts, as stated above, are to be considered as included in this invention.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulation is merely combinations of the active ingredient mentioned with pharmaceutically inert carriers and the like.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The compounds of Formula I can be prepared by any of the following processes which are depicted by four chemical reaction schemes.

In all four reaction schemes R, $R^1$, $R^2$, $R^3$, $R^4$, $R^5$, X and Y are the same as is defined for Formulae I and II.

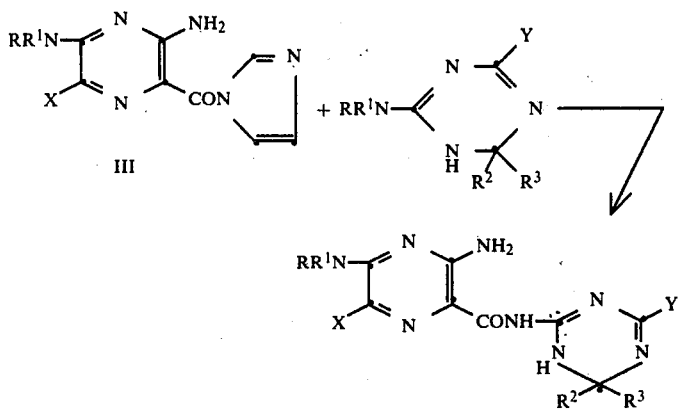

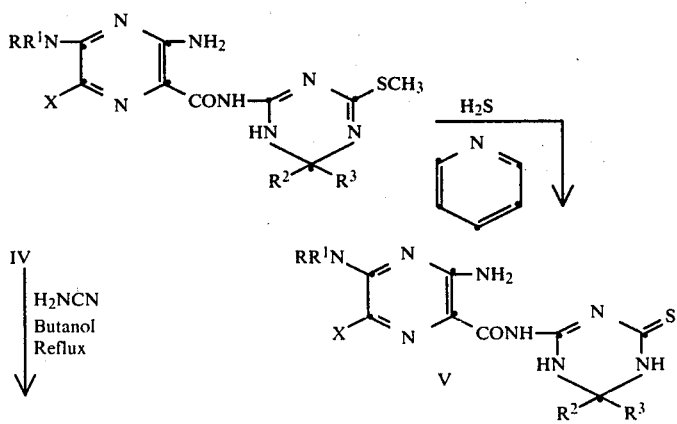

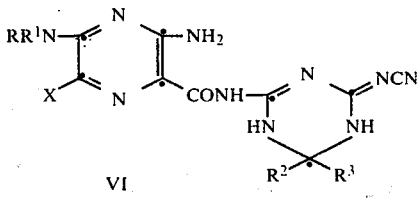

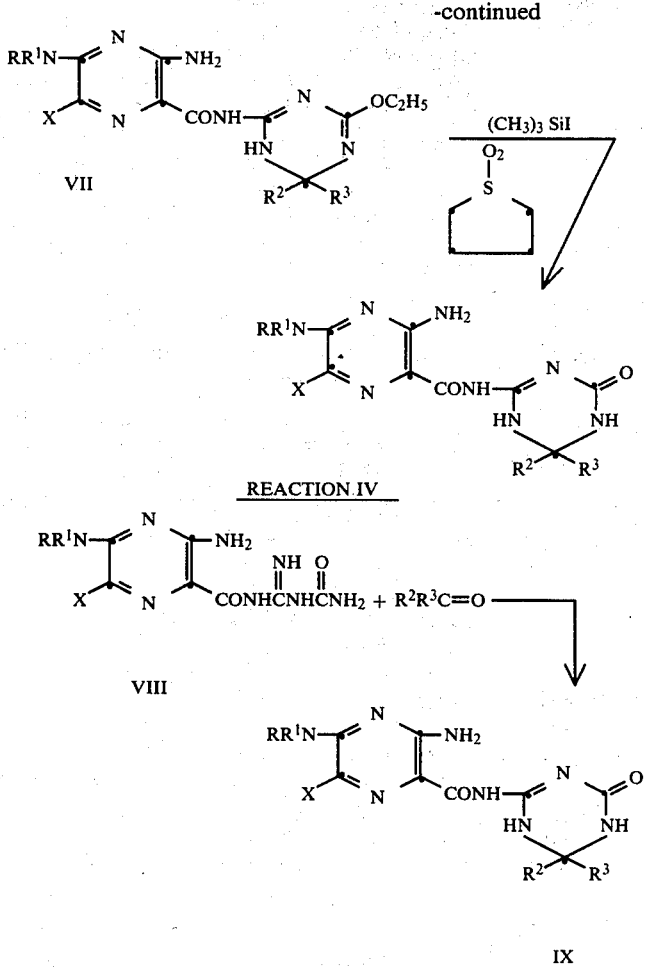

The process in Reaction I involves reacting an active pyrazinoic acid amide such as the imidazole amide III with a 2-amino-3,4-dihydro-1,3,5-triazine to obtain the desired product. The reaction is conducted in a suitable solvent such as dimethylformamide, dimethylsulfoxide and the like at a temperature of from 25° C. to the boiling temperature of the solvent but preferably from 50° C. to 100° C. The reaction is usually conducted with an excess of the triazine component and the desired product is isolated by filtration of the cooled reaction or by treatment of the reaction solution with water followed by filtration of the product.

In Reaction II, the methylthio triazine carboxamide starting material IV is reacted with hydrogen sulfide gas in an organic solvent such as pyridine at a temperature of from 0°–50° C. for a period of 1–24 hours. The end product V is isolated from the reaction mixture by known means such as for example by treating the reaction mixture with water.

Similarly, the starting material IV can be dissolved in a solvent such as butanol and reacted with H₂NCN to yield the product shown as Compound VI in Reaction Scheme II. This reaction is generally carried out at a temperature of 50° to reflux temperature of the solvent for a time of about 1–24 hours. The product VI is isolated by known means such as for example by cooling the reaction and filtering the product.

In Reaction III, the 6-ethoxy triazine carboxamide starting material VII is reacted with trimethyl silyl iodide in an organic solvent such as sulfolane at a temperature of from 25°–100° C. for a period of from 1–24 hours to yield 6-oxo triazine pyrazine carboxamide compounds.

Finally in Reaction IV starting material VIII is reacted with a ketone in a solvent such as dimethylformamide at 50° to reflux temperature of solvent for 1–24 hours to yield a similar 6-oxo end product shown as Compound IX.

The following examples are included to illustrate the preparation of compounds of this invention and also to illustrate the preparation of a representative dosage form.

EXAMPLE 1

3,5-Diamino-6-chloro-N-(3,4-dihydro-4,4-dimethyl-6-methylthio-1,3,5-triazin-2-yl)-2-pyrazinecarboxamide To a solution of 3,5-diamino-6-chloropyrazinoic acid (1.13 g., 0.006 mole) in dimethylformamide (50 ml.) is added 1,1'-carbonyldiimidazole (0.972 g., 0.006 mole). The reaction mixture is stirred for 1 hour in a nitrogen atmosphere to form, in situ, 1-(3,5-diamino-6-chloropyrazinoyl)imidazole, which is treated with 2-amino-3,4-dihydro-4,4-dimethyl-6-methylthio-1,3,5-triazine. The reaction mixture is heated at 95° for 3 hours and cooled to give 1.3 g. of 3,5-diamino-6-chloro-N-(3,4-dihydro-4,4-dimethyl-6-methylthio-1,3,5-triazin-2-yl)-2-pyrazinecarboxamide which melts at 232°–4° C.

Elemental analysis for $C_{11}H_{15}ClN_8OS$: Calcd: C, 38.54; H, 4.41; N, 32.69; Found: C, 38.39; H, 4.48; N, 32.64.

EXAMPLE 2

3,5-Diamino-6-chloro-N-(3,4-dihydro-4,4-dimethyl-6-mercapto-1,3,5-triazin-2-yl)-2-pyrazinecarboxamide hydrochloride Hydrogen sulfide is slowly bubbled with a solution of 3,5-diamino-6-chloro-N-(3,4-dihydro-4,4-dimethyl-6-methylthio-1,3,5-triazin-2-yl)-2-pyrazinecarboxamide (1.0 g., 0.0029 mole) in pyridine (25 ml.) containing triethylamine (1.5 ml.) for a period of five hours. Nitrogen is bubbled into the reaction mixture to remove excess hydrogen sulfide which is then poured into ice water (100 ml.). The collected solid is dissolved in hot water (75 ml.) containing hydrochloric acid (0.5 ml.) then cooled to give 3,5-diamino-6-chloro-N-(3,4-dihydro-4,4-dimethyl-6-mercapto-1,3,5-triazin-2-yl)-2-pyrazincarboxamide hydrochloride which melts at 232° C. with decomposition.

Elemental analysis for $C_{10}H_{13}ClN_8OS.HCl$ Calcd: C, 32.88; H, 3.86; N, 30.68; Found: C, 32.93; H, 4.42; N, 30.94.

EXAMPLE 3

3,5-Diamino-6-chloro-N-(3,4-dihydro-4,4-dimethyl-6-cyanoamino-1,3,5-triazin-2-yl)-2-pyrazinecarboxamide A solution of 3,5-diamino-6-chloro-N-(3,4-dihydro-4,4-dimethyl-6-methylthio-1,3,5-triazin-2-yl)-2-pyrazinecarboxamide (1.0 g., 0.0029 mol) and cyanamide (0.7 g., 0.017 mol) in 1-butanol (50 ml.) is heated at reflux for 5 hours. The 3,5-diamino-6-chloro-N-(3,4-dihydro-4,4-dimethyl-6-cyanoamino-1,3,5-triazin-2-yl)-2-pyrazinecarboxamide which separates melts at 342° C. with decomposition.

Elemental analysis for $C_{11}H_{10}ClN_{10}O$; Calcd: C, 39.23; H, 3.89; Cl, 10.53; Found: C, 39.32; H, 4.04; Cl, 10.65.

EXAMPLE 4

3,4-Diamino-6-chloro-N-(3,4-dihydro-4,4-dimethyl-6-ethoxy-1,3,5-triazin-2-yl)-2-pyrazinecarboxamide Step A:
2-Amino-3,4-dihydro-4,4-dimethyl-6-ethoxy-1,3,5-triazine To a solution of sodium (2.3 g., 0.1 gr. atom) in absolute ethanol (100 ml.) is added 2-amino-3,4-dihydro-4,4-dimethyl-6-methylthio-1,3,5-triazine (3.4 g., 0.02 mole) and the mixture is heated at reflux for 18 hours. The ethanol is distilled at reduced pressure and the residue dissolved in water (100 ml.) and extracted with ethyl acetate (3×100 ml.) dried over potassium carbonate and evaporated in vacuo to give 1.3 g of 2-amino-3,4-dihydro-4,4-dimethyl-6-ethoxy-1,3,5-triazine which melts at 175°-8° C. after crystallization from acetonitrile.

Elemental analysis for $C_7H_{14}N_4O$: Calcd: C, 49.39; H, 8.29; N, 32.92; Found: C, 48.84; H, 8.47; N, 33.42.

EXAMPLE 5

3,5-Diamino-6-chloro-N-(3,4-dihydro-4,4-dimethyl-6-hydroxy-1,3,5-triazin-2-yl)-2-pyrazinecarboxamide To a stirred solution of 3,5-diamino-6-chloro-N-(3,4-dihydro-4,4-dimethyl-6-ethoxy-1,3,5-triazin-2-yl)-2-pyrazinecarboxamide (0.55 g., 0.0016 mole) in sulfolane (10 ml.) is added trimethylsilyl iodide (1.5 ml.). The reaction mixture is stirred for 5 hours at 45° C., poured into ice water (30 ml.) containing hydrochloric acid (1.5 ml.), then extracted with chloroform (2×15 ml.) The aqueous layer is made basic with ammonia to give 420 mg. of 3,5-diamino-6-chloro-N-(3,4-dihydro-4,4-dimethyl-6-hydroxy-1,3,5-triazin-2-yl)-2-pyrazinecarboxamide which melts at 266°-8° C. after reprecipitation from dilute hydrochloric acid with ammonia.

Elemental analysis for $C_{10}H_{13}ClN_8O_2$; Calcd: C, 38.41; H, 4.19; N, 35.83; Found: C, 38.40; H, 4.25; N, 35.44.

EXAMPLE 6

3,5-Diamino-6-chloro-N-(3,4-dihydro-4,4-dimethyl-6-hydroxy-1,3,5-triazin-2-yl)-2-pyrazinecarboxamide Step A:
2-Amino-3,4-dihydro-4,4-dimethyl-6-hydroxy-1,3,5-triazine To a solution of 2-amino-3,4-dihydro-4,4-dimethyl-6-ethoxy-1,3,5-triazine (2.2 g.) in sulfolane (30 ml.) is added trimethylsilyl iodide (12 ml.). The reaction mixture is heated at 50° C. for four hours then poured into 50 ml of ice water containing 2 ml. of conc. HCl. The solution is extracted with chloroform then the aqueous layer is distilled in vacuo to a viscous syrup which upon treatment with 2-propanol and cooling deposits 2.1 g. of product hydrochloride which is dissolved in 3 ml. of water and treated with 2 ml. of conc. ammonia to give 1.1 g. of 2-amino-3,4-dihydro-4,4-dimethyl-6-hydroxy-1,3,5-triazine which melts above 300° C.

Elemental Analysis for $C_5H_{10}N_4O$: Calc.: C, 42.24; H, 7.09; N, 39.41; Found: C, 42.10; H, 7.51; N, 39.20.

Step B:
3,5-Diamino-6-chloro-N-(3,4-dihydro-4,4-dimethyl-6-hydroxy-1,3,5-triazin-2-yl)-2-pyrazinecarboxamide To a solution of 3,5-diamino-6-chloropyrazinoic acid (0.92 g., 0.0049 mole) in dimethylformamide (40 ml.) is added 1,1'-carbonyldiimidazole (0.80 g., 0.0049 mol). The reaction mixture is stirred for 2 hours in a nitrogen atmosphere to form, in situ, 1-(3,5-diamino-6-chloropyrazinoyl) imidazole which is treated with 2-amino-3,4-dihydro, 4,4-dimethyl-6-hydroxy-1,3,5-triazine (1.1 g., 0.0076 mole). The reaction mixture is heated for 3 hours at 95° C., and treated with ice to give 1.3 g. of 3,5-diamino-6-chloro-N-(3,4-dihydro-4,4-dimethyl-6-hydroxy-1,3,5-triazin-2-yl)-2-pyrazinecarboxamide which melts at 266°-8° C.

Elemental analysis for $C_{10}H_{17}ClN_8O_2$; Calc: C, 38.41; H, 4.19; N, 35.83; Found: C, 38.12; H, 4.51; N, 34.89.

EXAMPLE 7

3,5-Diamino-6-chloro-N-(3',4'-dihydro-6'-hydroxy-4-methylspirocyclohexane[1,4']-1,3,5-triazin-2-yl)-2-pyrazinecarboxamide A solution of 3,5-diamino-6-chloro-N-[[(aminocarbonyl)amino]iminomethyl]-2-pyrazinecarboxamide (0.5 g., 0.0018 mole) and 4-methylcyclohexanone (0.5 ml.) in dimethylformamide (10 ml.) is heated at 95° C. for 20 hours. The reaction mixture is treated with 20 ml. of 2-propanol, filtered, the filtrate distilled at reduced pressure to a volume of 2 ml. and chromatographed on silica gel to give 3,5-diamino-6-chloro-N-(3',4'-dihydro-6'-hydroxy-4-methylspirocyclohexane]1,4']-1,3,5-triazin-2-yl)-2-pyrazinecarboxamide which melts at 274° C.

Elemental analysis for $C_{14}H_{19}ClN_8O_2$: Calc.: C, 45.84; H, 5.22; Cl, 9.67; Found: C, 45.40; H, 5.17; Cl, 9.63.

EXAMPLE 8

Compressed Tablet containing 50 mg. of active ingredient.

|  | Per Tablet, Mg. |
|---|---|
| 3,5-diamino-6-chloro-N-(3,4-dihydro-4,4-dimethyl-6-methyl-thio-1,3,5-triazin-2-yl)-2-pyrazinecarboxamide | 50 |
| Calcium phosphate dibasic | 200 |
| Ethyl cellulose (as 5% solution in ethanol) | 5 |
| Unmixed granulation | 255 |
| Add: | |
| Starch, corn | 14 |
| Magnesium stearate | 1 |
|  | 270 |

Directions: Mix the active ingredient above and calcium phosphate and reduce to a No. 60 mesh powder. Granulate with Ethocel in alcohol and pass the wet granulation through a No. 10 screen. Dry the granulation at 110° F. for 12-18 hours. Dry grind to a No. 20 mesh. Incorporate the "adds" and compress into tablets each weighing 270 mg.

EXAMPLE 9

Dry filled capsule containing 50 mg. of active ingredient.

|  | Per capsule, mg. |
|---|---|
| 3,5-diamino-6-chloro-N-(3,4-dihydro-4,4-dimethyl-6-mercapto 1,3,5-triazin-2-yl)-2-pyrazine-carboxamide hydrochloride | 50 |
| Lactose | 273 |
| Magnesium stearate | 2 |
| Mixed powders | 325 |

Mix the active ingredient above, lactose, and magnesium stearate and reduce to a No. 60 mesh powder. Encapsulate, filling 325 mg. in each No. 2 capsule.

The above formulations can be employed to prepare compressed tablets or capsules of other novel compounds of this invention hereinbefore described.

EXAMPLE 10

Combination dosage form in dry filled capsule

|  | Per capsule, mg. |
|---|---|
| 3,5-diamino-6-chloro-N-(3,4-dihydro-4,4-dimethyl-6-cyano-amino-1,3,5-triazin-2-yl)-2-pyrazinecarboxamide | 50 |
| Magnesium stearate | 2 |
| Lactose | 223 |
| Mixed powders | 275 |

Mix all of the above ingredients, reduce to a No. 60 mesh powder and encapsulate, filling 275 mg. in each No. 2 capsule.

The above examples describe the preparation of certain compounds which are illustrative of the novel compounds of this invention, and certain specific dosage forms suitable for administering the novel compounds, it is to be understood that the invention is not to be limited to the specific compounds described in the examples or by the specific reaction conditions described for the preparation of these compounds or by the specific ingredients included in the pharmaceutical preparations, but is to be understood to embrace variations and modifications thereof which fall within the scope of the appended claims.

What is claimed is:

1. A compound of the formula or the tautomeric form thereof wherein

R is hydrogen, $C_{1-5}$ alkyl, $C_{2-5}$ alkenyl or $C_{3-6}$ cycloalkyl;

$R^1$ is hydrogen, $C_{1-5}$ alkyl, $C_{2-5}$ alkenyl or $C_{3-6}$ cycloalkyl;

$R^2$ is $C_{1-5}$ alkyl;

$R^3$ is $C_{1-5}$ alkyl;

$R^2$ and $R^3$ can be joined with the carbon atom to which they are attached to form a 3-7 membered carbon ring;

X is halo;

Y is OH, SH, $C_{1-5}$ alkoxy, $C_{1-5}$ alkylthio and $NR^4R^5$ wherein $R^4$ is hydrogen or $C_{1-5}$ alkyl and $R^5$ is hydrogen, $C_{1-5}$ alkyl, CN, $CONH_2$, $$\overset{CNH_2}{\underset{NH}{\|}},$$

$NO_2$ or $NH_2$ and the pharmaceutical acid addition salts thereof.

2. A compound of the formula wherein

R is hydrogen or $C_{1-5}$ alkyl, $R^1$ is hydrogen or $C_{1-5}$ alkyl, $R^2$ is methyl, $R^3$ is methyl, X is chloro, Y is OH, SH, $C_{1-5}$ alkoxy, $C_{1-5}$ alkylthio or cyanoamino and the pharmaceutically acceptable salts thereof.

3. A compound of claim 2 which is 3,5-diamino-6-chloro-N-(3,4-dihydro-4,4-dimethyl-6-methylthio-1,3,5-triazin-2-yl)-2-pyrazinecarboxamide.

4. A compound of claim 2 which is 3,5-diamino-6-chloro-N-(3,4-dihydro-4,4-dimethyl-6-mercapto-1,3,5-triazin-2-yl)-2-pyrazinecarboxamide hydrochloride.

5. A compound of claim 2 which is 3,5-diamino-6-chloro-N-(3,4-dihydro-4,4-dimethyl-6-cyanoamino-1,3,5-triazin-2-yl)-2-pyrazinecarboxamide.

6. A compound of claim 2 which is 3,5-diamino-6-chloro-N-(3,4-dihydro-4,4-dimethyl-6-ethoxy-1,3,5-triazin-2-yl)-2-pyrazinecarboxamide.

7. A compound of claim 2 which is 3,5-diamino-6-chloro-N-(3,4-dihydro-4,4-dimethyl-6-hydroxy-1,3,5-triazin-2-yl)-2-pyrazinecarboxamide.

8. A pharmaceutical composition useful in the treatment of edema and hypertension which comprises in combination with a pharmaceutically acceptable carrier, a compound or the tautomeric form of the formula:

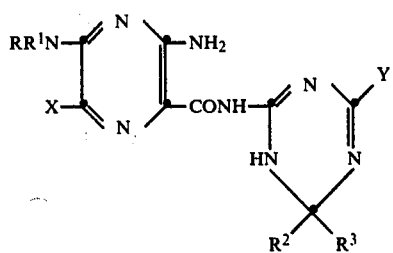

wherein
R is hydrogen, $C_{1-5}$ alkyl, $C_{2-5}$ alkenyl or $C_{3-6}$ cycloalkyl;
$R^1$ is hydrogen, $C_{1-5}$ alkyl, $C_{2-5}$ alkenyl or $C_{3-6}$ cycloalkyl;
$R^2$ is $C_{1-5}$ alkyl;
$R^3$ is $C_{1-5}$ alkyl;
$R^2$ and $R^3$ can be joined with the carbon atom to which they are attached to form a 3–7 membered carbon ring;
X is halo;
Y is OH, SH, $C_{1-5}$ alkoxy, $C_{1-5}$ alkylthio and $NR^4R^5$ wherein $R^4$ is hydrogen or $C_{1-5}$ alkyl and $R^5$ is hydrogen, $C_{1-5}$ alkyl, CN, $CONH_2$,

$NO_2$ or $NH_2$ and the pharmaceutical acid addition salts thereof.

9. A pharmaceutical composition useful in the treatment of edema and hypertension which comprises in combination with a pharmaceutically acceptable carrier, a compound or the tautomeric form of the formula:

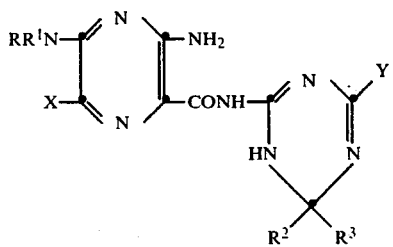

wherein
R is hydrogen or $C_{1-5}$ alkyl,
$R^1$ is hydrogen or $C_{1-5}$ alkyl,
$R^2$ is methyl,
$R^3$ is methyl,
X is chloro,
Y is OH, SH, $C_{1-5}$ alkoxy, $C_{1-5}$ alkylthio or cyanoamino and the pharmaceutically acceptable salts thereof.

10. A method of treating edema or hypertension which comprises administering to a patient in need of such treatment a pharmaceutically effective amount of a compound of the formula:

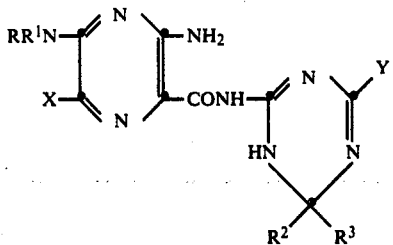

wherein
R is hydrogen, $C_{1-5}$ alkyl, $C_{2-5}$ alkenyl or $C_{3-6}$ cycloalkyl;
$R^1$ is hydrogen, $C_{1-5}$ alkyl, $C_{2-5}$ alkenyl or $C_{3-6}$ cycloalkyl;
$R^2$ is $C_{1-5}$ alkyl;
$R^3$ is $C_{1-5}$ alkyl;
$R^2$ and $R^3$ can be joined with the carbon atom to which they are attached to form a 3–7 membered carbon ring;
X is halo;
Y is OH, SH, $C_{1-5}$ alkoxy, $C_{1-5}$ alkylthio and $NR^4R^5$ wherein $R^4$ is hydrogen or $C_{1-5}$ alkyl and $R^5$ is hydrogen, $C_{1-5}$ alkyl, CN, $CONH_2$,

$NO_2$ or $NH_2$ and the pharmaceutical acid addition salts thereof.

11. A method of treating edema or hypertension which comprises administering to a patient in need of such treatment a pharmaceutically effective amount of a compound of the formula:

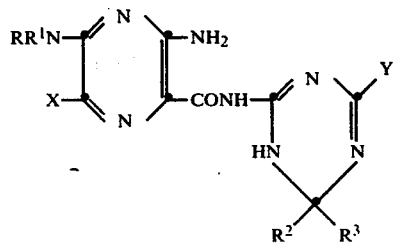

wherein
R is hydrogen or $C_{1-5}$ alkyl,
$R^1$ is hydrogen or $C_{1-5}$ alkyl,
$R^2$ is methyl,
$R^3$ is methyl,
X is chloro,
Y is OH, SH, $C_{1-5}$ alkoxy, $C_{1-5}$ alkylthio or cyanoamino and the pharmaceutically acceptable salts thereof.

* * * * *